United States Patent [19]

McRae

[11] Patent Number: Plant 5,960

[45] Date of Patent: Apr. 28, 1987

[54] ASIATIC LILY NAMED 'CORDELIA'

[75] Inventor: Edward A. McRae, Boring, Oreg.

[73] Assignee: Melridge, Inc., Gresham, Oreg.

[21] Appl. No.: 710,577

[22] Filed: Mar. 11, 1985

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler; John B. Lungmus

[57] ABSTRACT

A new variety of Asiatic hybrid lily having flowers of large size, excellent form, and an intense and unusual color pattern comprising an unusual combination of yellow and gold color tones with relatively sparse maculation, this color pattern being new in the upright Asiatic division of lilies. This plant is highly resistant to disease and shows high tolerance to virus and its flowers have long persistence, both on the plant and as cut-flowers, making it an excellent garden plant. Also, the bulbs may be precooled and forced for cut-flower production, the flowers being produced in late mid-season, inbetween the flowering times of its siblings of similar appearance, thereby broadening the season of cut-flower production.

1 Drawing Figure

BACKGROUND OF THE INVENTION

This new variety of lily plant originated as a seedling selected from a group of seedlings resulting from my crossing a plant of the species *Lilium Wilsonii* var. "*flavum*" and the cultivar "Connecticut King" (unpatented) at Sandy, Oreg. This crossing was done as the result of breeding efforts carried on by me since the year 1971 with the object of producing superior upright-flowering Asiatic lilies in the shades of yellow and gold, suited to cut-flower production, and representing a range of flowering times so as to extend the season of cut-flower production.

The flowers of this new lily plant are characterized by large size, very broad tepals of thick texture, and an unusual color pattern, each yellow tepal being flushed with gold at its base and having comparatively sparse spotting appearing on each side of the nectaries at their outer end near the base of the tepal. This seedling was selected because the plant and its flowers appeared to possess all of the desired characteristics of form, color, and habit.

This new variety of lily plant has been asexually reproduced by me and under my direction at Sandy, Oreg., and successive generations produced by bulb-scale propagation and natural propagation from bulblets have shown that this new plant possesses the desirable characteristics of hybrid vigor, great hardiness, and a high degree of disease resistance as observed at Sandy, Oreg., and successive generations produced by bulb-scale propagation and natural propagation from bulblets have demonstrated that the novel and distinctive characteristics of this new variety hold true under asexual propagation from generation to generation and appear to be firmly fixed.

DESCRIPTION OF THE DRAWING

My new variety of lily plant is illustrated in the accompanying photographic drawing which shows an open bloom illustrating the flower form, the tepal arrangement, and the unusually broad form of the tepals, the flower portion of the view having been hand-painted to show the novel and distinctive yellow and gold color pattern as herein specified and the relatively sparse maculation, particularly on the outer tepals.

DESCRIPTION OF THE NEW VARIETY PLANT

The following is a detailed description of my new variety of Asiatic hybrid lily with color designations according to The R.H.S. Colour Chart published by The Royal Horticultural Society of London, England, as observed at Sandy Oreg., and with nomenclature according to The International Lily Register, 2nd edition, of The Royal Horticultural Society.

THE PLANT

Origin: Seedling.

Parentage:

*Seed parent.*—*Lilium Wilsonii* var. "*flavum*" (unpatened).

*Pollen parents.*—"Connecticut King" (unpatented).

Classification:

*Botanic.*—Hybrid lily cultivar, Division I-A of The Horticultural Classification of Lilies by The Royal Horticultural Society.

*Commercial.*—Upright Asiatic hybrid lily.

Form: Single stem, erect and stately.

Height: About 120 to 170 cm. from bulbs about 15 to 20 cm. in circumference.

Growth: Vigorous and upright.

Foliage:

*Quantity.*—Abundant.

*Leaf size.*—About 8 to 12 cm. long and about 1.5 to 2 cm. wide at the base.

*Leaf shape.*—Lanceolate and sessile.

*Texture.*—Leathery.

*Aspect.*—Glossy.

*Color.*—Medium green.

Bulbs:

*Size.*—Ranging to 25 cm. in circumference in commercial use.

*Color.*—White.

THE BUD

Form: Long oblong with obtuse base and tip.

Size: About 7 to 9 cm. long just prior to opening.

Opening rate: The bud opens slowly at maturity taking about one hour in response to light.

Color: Medium to deep yellow when the outer tepals first divide and when the tepals begin to unfurl.

Peduncle:

*Length.*—About 7 to 10 cm. depending upon light levels.

*Color.*—Medium green.

THE FLOWER

Blooming habit: Once annually in late mid-season for Asiatic lilies. October-dug bulbs, properly cooled, planted in February in western Oregon, under glass and with no supplementary lighting, will flower in an average of from 95 to 100 days.

Size: Large; 15 to 18 cm. in diameter.

Borne: About 5 to 8 on a single stem as a compact raceme.

Shape: Flat to slightly cup-shaped with the tepal tips lightly recurved.

Tepalage:

*Number.*—Six.

*Arrangement.*—Outer tepals appearing between the inner tepals and slightly overlapping them.

*Color.*—The flowers are distinguished by their color pattern, the base color being Yellow, R.H.S. 12A, and each tepal having a flush of Gold, R.H.S. 21A, about 2 cm. wide and about 2 cm. long above the nectary and along the tepal midrib, the flowers carrying a small cluster of deep magenta colored spots on each side of the nectary adjacent its outer end.

*Color change.*—As the flowers age, the color intensifies slightly and may become more golden toned under low light levels.

*Tepal longetivity.*—The tepals stay on the stem about 3 weeks.

Pedicels:

*Length.*—About 4 to 6 cm.

*Form.*—Sturdy and upright.

*Color.*—Light green.

Fragrance: None.

Lasting quality: The flower is long lasting, both on the plant and as a cut flower.

Disease resistance: The flower and plant are resistant to disease and are particularly resistant to Fusarium and Botrytis, as observed in the region of western Oregon.

THE REPRODUCTIVE ORGANS

Stamens:

*Number.*—Six.

*Arrangement.*—Typical of genus Lilium.

Anthers:

*Color.*—Greyed Gold, R.H.S. 167A.

Filaments:

*Length.*—About 5 cm.

*Color.*—Ivory or yellow.

Pollen:

*Color.*—Same as anthers.

Pistils:

*Number.*—One.

Style:

*Length.*—About 5 cm.

Stigma: Light plum to gold in color.

Character of ovary: Typical of genus Lilium.

THE FRUIT

Fertility: The fruit is fertile.

Shape: Ovoid.

Color at maturity: Soft brown, sometimes overlaid with light plum.

This new variety of Asiatic hybrid lily most nearly resembles "Connecticut King", as does its companion "Vanessa." The Flowers of this new variety differ from those of "Vanessa", however, in that the tepals are more widely spaced and are of a generally more oblanceolate shape than those of "Vanessa" and the upper tepals very narrowly overlap the margins of the lower tepals appearing in the pattern of a six-pointed star, thus making the flower of the new plant much more open in form with the nectaries of all of the tepals being spaced apart at the base end of the flower rather than overlapping as in the case of "Vanessa", thus providing a flower form much different than that of "Vanessa". Also, in the new flower, the stamens are bunched above the center of the flower rather than being widely spaced as in the case of "Vanessa".

Distinguishing Characteristics of Siblings From the Cross *Lilium Wilsonii* var. *flavum* × "Connecticut King"

| Cv | Days to Bloom | Buds | Maculation |
|---|---|---|---|
| Pollyanna Serial No. 710,427 | 80–85 | 5–8 | Heavy, large. |
| Joanna Serial No. 710,457 | 80 | 5–7 | Light |
| Adelina Serial No. 710,614 | 80–85 | 6–8 | Very few and small. Of deep magenta color. |
| Vanessa Serial No. 710,496 | 90–95 | 5–8 | Very light |
| Yolanda Serial No. 710,577 | 95–100 | 5–8 | Sparse and of deep magenta color. |
| Gold Medal (Half Sib) Serial No. 710,592) | 60–70 | 6–8 | Few tiny |

| Cv | Other Notable Characteristics |
|---|---|
| Pollyanna Serial No. 710,427 | Relatively narrow, widely spaced tepals and sepals with very little marginal overlapping. Arrangement, hexagonal. |
| Joanna Serial No. 710,457 | Tepal-sepal angle 60°. Arrangement, generally imbricated. |
| Adelina Serial No. 710,614 | Tepals are large, thick textured, relatively broad, and with lightly recurved tips. Arrangement, imbricated. |
| Vanessa Serial No. 710,496 | Tepals have slightly recurved tips and inconspicuous maculation. Arrangement, uniformly imbricated. |
| Yolanda Serial No. 710,577 | Larger bulb, flower dished with tepal-sepal angle 60°, with lightly overlapping arrangement. |
| Gold Medal (Half Sib) Serial No. 710,592) | Very thick and broad tepals in 60° overlapping arrangement with sepals, Unusually long lasting flowers, bud blast resistant when forced, and attains large bulb size only in season. |

I claim:

1. A new and distinct variety of Asiatic hybrid lily, substantially as herein shown and described, characterized by its open flower form wherein the generally oblanceolate upper tepals extend midway between the lower tepals with very little overlapping of the tepal margins and with their nectary ends openly spaced apart at the base of the flower.

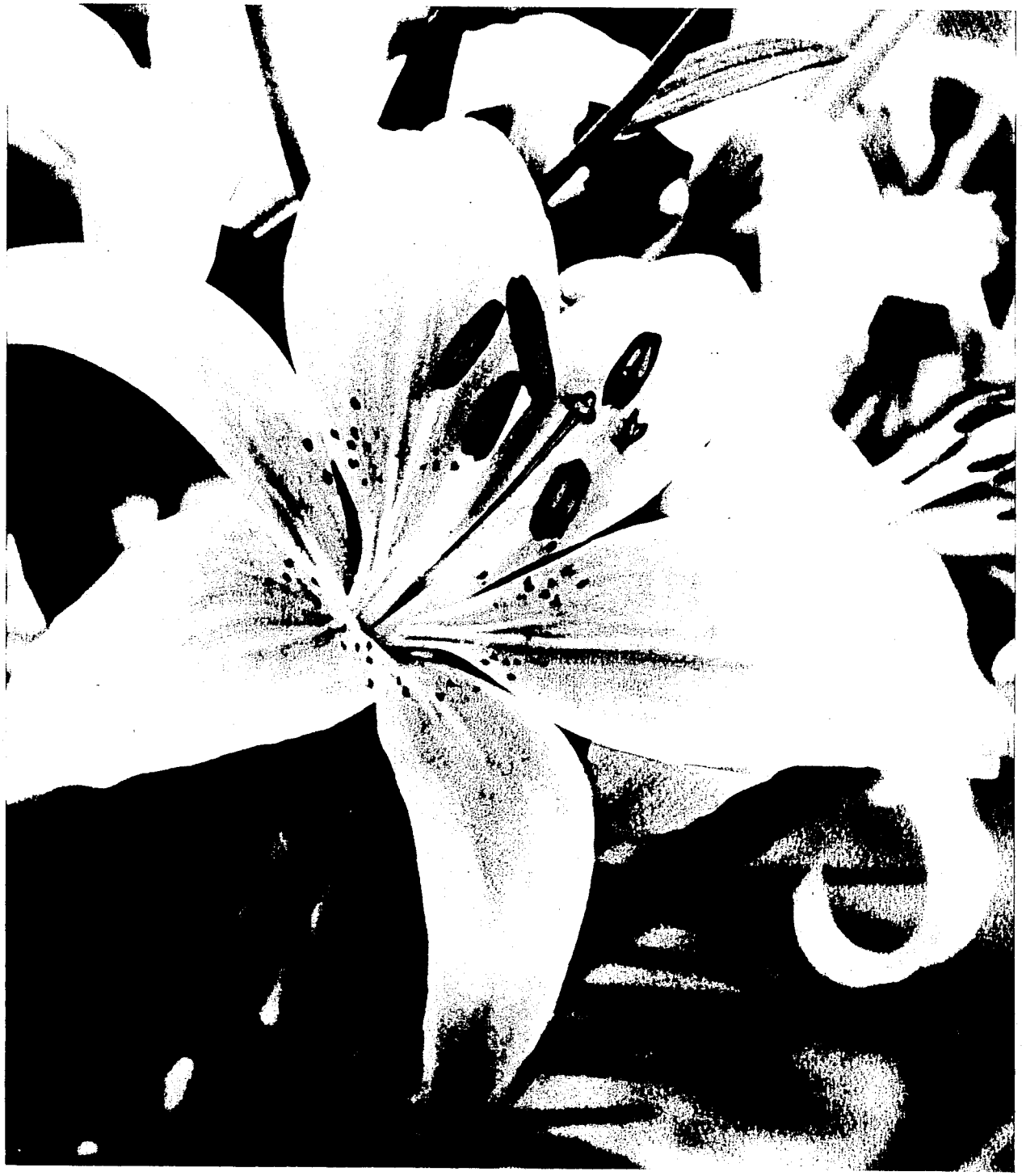

* * * * *